(12) United States Patent
Tanno et al.

(10) Patent No.: US 10,272,625 B2
(45) Date of Patent: Apr. 30, 2019

(54) PNEUMATIC TIRE AND METHOD OF MANUFACTURING THE SAME

(71) Applicant: The Yokohama Rubber Co., LTD., Minato-ku, Tokyo (JP)

(72) Inventors: Atsushi Tanno, Hiratsuka (JP); Hayato Sakamoto, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 392 days.

(21) Appl. No.: 15/024,781

(22) PCT Filed: Apr. 15, 2014

(86) PCT No.: PCT/JP2014/060735
§ 371 (c)(1),
(2) Date: Mar. 24, 2016

(87) PCT Pub. No.: WO2015/045459
PCT Pub. Date: Apr. 2, 2015

(65) Prior Publication Data
US 2016/0229140 A1 Aug. 11, 2016

(30) Foreign Application Priority Data
Sep. 24, 2013 (JP) .................................. 2013-196852

(51) Int. Cl.
*B60C 23/00* (2006.01)
*B60C 19/00* (2006.01)
(Continued)

(52) U.S. Cl.
CPC ......... *B29D 30/0061* (2013.01); *B29D 30/02* (2013.01); *B29D 30/0601* (2013.01);
(Continued)

(58) Field of Classification Search
CPC ..... B60C 19/00; B60C 23/00; B60C 23/0491; B60C 23/0493; B29D 30/06; B29D 30/0633; B29D 203/0638; B29D 203/0683
See application file for complete search history.

(56) References Cited

U.S. PATENT DOCUMENTS
2003/0155054 A1  8/2003  Bell
2006/0260726 A1  11/2006 Bell
(Continued)

FOREIGN PATENT DOCUMENTS
EP     2460673     *   7/2013
JP     H02-071327      5/1990
(Continued)

OTHER PUBLICATIONS
International Search Report for International Application No. PCT/JP2014/060735 dated Jul. 15, 2014, 4 pages, Japan.

*Primary Examiner* — Justin R Fischer
(74) *Attorney, Agent, or Firm* — Thorpe North & Western

(57) ABSTRACT

The present technology provides a pneumatic tire provided with a mechanical fastener member for attaching an object to the inner surface of a pneumatic tire, wherein the mechanical fastener member is bonded with high bonding strength to the inner circumferential surface of the tire, and a method of manufacturing the same. The pneumatic tire of the present technology comprises a mechanical fastener member on a tire inner surface, the mechanical fastener member corresponding to a first member of a mechanical fastener separable into two members and being fixed protruding to a tire cavity side. A fixing strength of the mechanical fastener member is from 0.1 to 100 (N/mm$^2$).

18 Claims, 15 Drawing Sheets

(51) Int. Cl.
   *B29D 30/06* (2006.01)
   *B29D 30/20* (2006.01)
   *B29D 30/00* (2006.01)
   *B60C 17/04* (2006.01)
   *B60C 23/04* (2006.01)
   *B29D 30/02* (2006.01)
   *G01N 21/33* (2006.01)

(52) U.S. Cl.
   CPC .......... *B29D 30/0662* (2013.01); *B60C 17/04* (2013.01); *B60C 19/00* (2013.01); *B60C 19/002* (2013.01); *B60C 19/003* (2013.01); *B60C 23/00* (2013.01); *B60C 23/0493* (2013.01); *G01N 21/33* (2013.01); *B29D 2030/0072* (2013.01); *B60C 2019/004* (2013.01)

(56) References Cited

U.S. PATENT DOCUMENTS

| | | |
|---|---|---|
| 2009/0159172 A1 | 6/2009 | Tanno et al. |
| 2010/0108222 A1 | 5/2010 | Bell |
| 2010/0230024 A1 | 9/2010 | Borot et al. |
| 2011/0113630 A1 | 5/2011 | Bell |
| 2012/0024439 A1 | 2/2012 | Tanno et al. |
| 2012/0298272 A1 | 11/2012 | Tanno et al. |
| 2013/0248071 A1 | 9/2013 | Tanno et al. |
| 2014/0041165 A1 | 2/2014 | Momose et al. |
| 2014/0144564 A1 | 5/2014 | Borot et al. |
| 2014/0150946 A1 | 6/2014 | Joza et al. |
| 2016/0375734 A1 | 12/2016 | Borot et al. |

FOREIGN PATENT DOCUMENTS

| | | |
|---|---|---|
| JP | H04-030907 | 7/1992 |
| JP | H11-0164722 | 6/1999 |
| JP | 2005-517581 | 6/2005 |
| JP | 2006-044503 | 2/2006 |
| JP | 2010-264147 | 11/2010 |
| JP | 2012-025318 | 2/2012 |
| JP | 2012-025319 | 2/2012 |
| JP | 2012-240465 | 12/2012 |
| JP | 2012-240603 | 12/2012 |
| JP | 2013-022819 | 2/2013 |
| WO | WO 2009/013269 | 1/2009 |
| WO | WO 2012/144367 | 10/2012 |
| WO | WO 2013/012062 | 1/2013 |

* cited by examiner

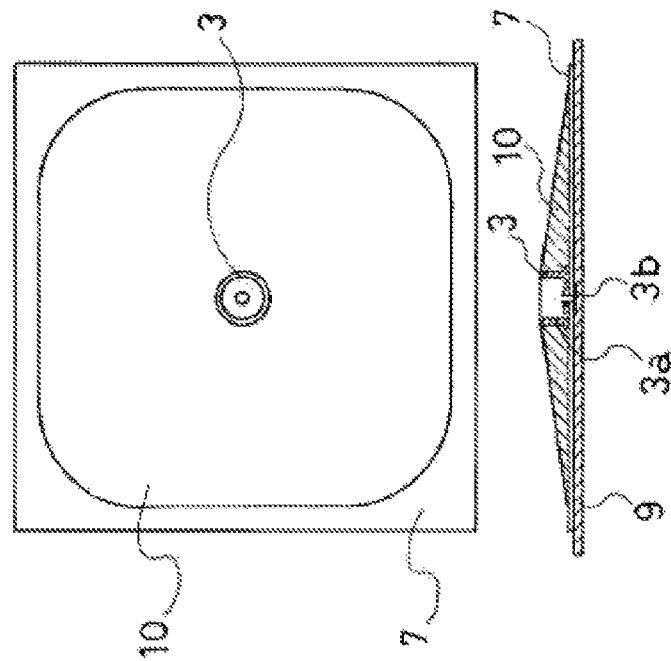
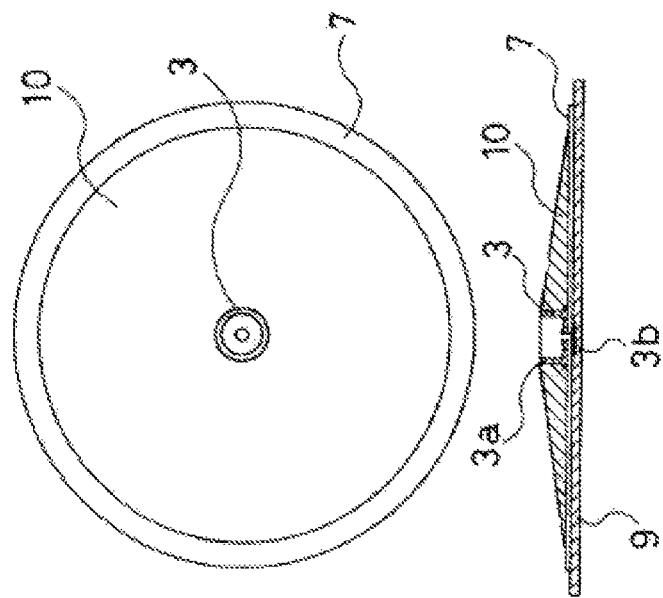
FIG. 9A
FIG. 9B

PNEUMATIC TIRE AND METHOD OF MANUFACTURING THE SAME

TECHNICAL FIELD

The present technology relates to a pneumatic tire and a method of manufacturing the same.

The present technology further relates to a pneumatic tire provided with a mechanical fastener member for attaching an object to the inner surface of the pneumatic tire, in particular to a pneumatic tire in which such a mechanical fastener member is bonded to the tire inner circumferential surface with extremely high bonding strength, and a method of manufacturing the same.

BACKGROUND ART

In recent years, various research into disposing objects having various functions on an inner circumferential surface of a pneumatic tire has been conducted.

For example, an attaching method has been proposed in which tire tags (for example, radio frequency identification tags), chips, or the like are attached to the innerliner or the like of a raw tire using a surface fastener such as a hook and loop fastener, a hook and hook fastener, or the like (see Japanese Unexamined Patent Application Publication No. 2005-517581A).

Additionally, a pneumatic tire has been proposed in which a surface fastener is vulcanization bonded to a region of the tire inner surface corresponding to a tread portion, and a noise absorbing member is attached to the tire inner surface via the surface fastener (Japanese Unexamined Patent Application Publication No. 2006-44503A).

The surface fasteners proposed in Japanese Unexamined Patent Application Publication Nos. 2005-517581 and 2006-44503A have been preferable configurations in that relatively strong engagement force is realized when attaching, and engagement on a surface can be achieved without slight misalignments when attaching becoming a problem.

However, with surface fasteners, a state in which the individual engaging elements of the surface fastener are engaged with one another is not ideal due to the inner circumferential surface of the pneumatic tire being an annular, curved surface. With surface fasteners, portions of the edges and center portions become raised, and an amount of obtained engagement force varies (positional variation within the tire and variation from tire to tire). As a result, in some cases, the expected engagement force has not been obtained. Additionally, deterioration and/or declining over time of the engagement force of an entirety of the surface fastener accompanying the occurrence and progression of the partial physical deterioration occurs as a result of repetitive deformation and compaction over an extended period of time caused by rotation at high speeds in a state of relatively elevated temperatures. This has led to cases in which difficulties have been met in maintaining a desired engagement force over an extended period of time.

Furthermore, although surface fasteners have been preferable in that engagement on a surface can be achieved without slight misalignments when attaching becoming a problem, when the attached functional object is, for example, a measuring device, a way to more reliably and precisely attach the object to a position has been demanded. Because of this lack of reliable and precise attachment, there have been functional objects not suited to being attached with a surface fastener.

Also, the present inventors have previously proposed a pneumatic tire whereby a desired engagement force can be maintained over an extended period of time, the engagement force physically deteriorating or declining over time due to extreme usage conditions, including repetitive deformation and compaction over an extended period of time caused by tire rotation at high speeds in a state of relatively elevated temperatures, to a minimal degree. The obtained engagement force is great and is essentially free of variations in strength (positional variation within the tire and variation from tire to tire). Specifically, a pneumatic tire is proposed in which types of objects with desired functions are attached by bonding mechanical fasteners, known as hooks or snaps, to a tire inner surface (see Japanese Unexamined Patent Application Publication Nos. 2012-25318A, 2012-25319A or 2012-240465A).

As described in the scope of the claims of exemplary Japanese Unexamined Patent Application Publication No. 2012-25318A, specifically, a pneumatic tire is proposed provided with a first fastener of a separable pair of mechanical fasteners, such as hooks or snaps, on the tire inner surface (claim 1 of the scope of the claims of Japanese Unexamined Patent Application Publication No. 2012-25318A). More specifically, a pneumatic tire is proposed wherein the first fastener comprises at least two components, the two components being fixed together to form the first fastener by sandwiching a tire member or a tire reinforcing member (claim 2 of the scope of the claims of Japanese Unexamined Patent Application Publication No. 2012-25318A).

According to the methods described in Japanese Unexamined Patent Application Publication Nos. 2012-25318A, 2012-25319A and 2012-240465A of attaching a desired object by bonding a mechanical fastener (hooks or snaps) to a tire inner surface, an object can be engaged and attached to a tire inner surface via such a mechanical fastener. Also, according to the methods, the obtained engagement force is typically great and is essentially free of variations in strength (positional variation within the tire and variation from tire to tire). Furthermore, the object can be attached at a predetermined position in a precise manner. As a result, a superior pneumatic tire is achieved whereby a desired engagement force can be maintained over an extended period of time, the engagement force deteriorating or declining over time due to repetitive extreme usage conditions over an extended period of time to a minimal degree.

In particular, by using, as the first mechanical fastener attached to the tire inner surface, a fastener that comprises at least two components, the two components fixing together to form the first fastener by sandwiching a tire member or a tire reinforcing member, a more superior mechanical fastener with increased fixing strength and good durability is achieved.

However, with the configurations of the methods described above, when a large object is attached, the mechanical fastener may be required to be attached in a state protruding from the tire inner surface by a certain degree. Also, when a heavy object is attached, the bonding strength between the tire inner surface and the mechanical fastener may be insufficient.

Notably, when a comparatively large, heavy specific functional object is attached to a tire inner surface, in particular a curved tire inner circumferential surface, the mechanical fastener requires a large protruding height so that the object and the inner circumferential surface do not interfere with each other. Also, in the majority of cases in which only one mechanical fastener (one pair) is used to fasten, as the force applied upon fastening cannot be distributed, enhancing the fixing strength to the tire inner surface is desirable. In other words, in most cases, mechanical fasteners cannot be added to the configurations after the tire is formed, and because the configurations in essence use one fastener to fasten, a pair of fasteners is needed which can be applied to the attachment of each type of the functional objects, and if a plurality of fasteners are used for fastening, pairs that correspond in number and position on both sides including the side of each type of functional object to be attached. As a result, versatility is unfortunately decreased.

Moreover, Japanese Unexamined Patent Application Publication No. 2012-25318A describes a mechanical fastener preferably having a height of a portion that protrudes most from the tire inner surface from 0 mm to 3 mm (Japanese Unexamined Patent Application Publication No. 2012-25318A, paragraph [0029]). A fastener having a protruding height greater than that range is not recommended.

This may be because when a mechanical fastener has a large protruding height, the bonding strength and durability of the mechanical fastener itself may become insufficient, regardless of the dimensions, weight, and other characteristics of each type of the attached functional objects. In particular, the present inventors believe that a contributing factor to this is that when a mechanical fastener member with a large protruding height is provided, the actions and functions of the bladder are interrupted around the mechanical fastener member.

Two assumed factors arising when the protruding height is large are detailed below.

(a) Upon vulcanization, although the pressure applied to the vulcanization bladder transmits to the tire, the pressure is insufficiently applied to the tire at the portion where the fastener with a large protruding height is located due to a space (see space X of FIG. 3) forming between the fastener and the vulcanization bladder. As a result, the rubber is insufficiently vulcanized. Consequently, the strength of the rubber or rubberized filler where the fastener is embedded inside the tire decreases, causing the durability of the fastener to decrease.

(b) Upon initiation of the vulcanization of a tire, the vulcanization bladder develops (expands) inside the tire. However, when the surface of the bladder and the tire surface move and rub against each other in the surface direction, the fastener with a large protruding height is subject to lateral force in a specific direction and is not fixed in a straight manner. As a result, the durability of the fastener decreases.

SUMMARY

In light of the above, the present technology provides a pneumatic tire provided with a mechanical fastener member for attaching an object to the inner surface of a pneumatic tire, wherein the mechanical fastener member is bonded with extremely high bonding strength to the tire inner circumferential surface, and a method of manufacturing the same.

A pneumatic tire of the present technology has the configuration described in (1) below.

(1) A pneumatic tire comprising a mechanical fastener member on a tire inner surface, the mechanical fastener member corresponding to a first member of a mechanical fastener separable into two members, and the mechanical fastener member being fixed protruding to a tire cavity side. In such a pneumatic tire, the mechanical fastener member has a fixing strength of from 0.1 to 100 (N/mm$^2$).

The pneumatic tire according to the present technology is preferably configured as described in any of (2) to (12) below.

(2) The pneumatic tire according to the above-described (1), wherein a bottom portion of the mechanical fastener member is embedded in the tire inner surface, and the mechanical fastener member has a protruding height from the tire inner surface of 3 mm or greater and a maximum diameter of 8 mm or greater.

(3) The pneumatic tire according to the above-described (1) or (2), wherein a recess is formed in the tire inner surface around the mechanical fastener member.

(4) The pneumatic tire according to any one of the above-described (1) to (3), wherein the mechanical fastener member comprises two or more components, the two or more components forming the mechanical fastener member by being fixed together and sandwiching a tire member or a tire reinforcing member fixed to the tire; and the mechanical fastener member is fixed to the tire member or the tire reinforcing member fixed to the tire by vulcanization bonding.

(5) The pneumatic tire according to any one of the above-described (1) to (4), wherein the mechanical fastener member comprises the two or more components, the two or more components forming the mechanical fastener member by being fixed together and sandwiching the tire reinforcing member fixed to the tire; and the recess is formed in the tire inner surface around the mechanical fastener member, the entire recess being positioned within an outer edge line of the tire reinforcing member when the tire inner surface is viewed in plan from vertically above the tire inner surface.

(6) A pneumatic tire comprising a detachable collar member disposed around the mechanical fastener member of the pneumatic tire described in any one of the above-described (1) to (5) in a space formed between a protruding tip of the mechanical fastener member and a tire inner surface around the mechanical fastener member.

(7) The pneumatic tire according to the above-described (6), wherein the collar member is disposed prior to vulcanization molding of the pneumatic tire, and the pneumatic tire is vulcanization molded in a state in which the collar member is disposed therein.

(8) The pneumatic tire according to the above-described (6), wherein the other collar member is disposed in the space prior to vulcanization molding of the pneumatic tire and removed after vulcanization molding of the pneumatic tire, the collar member being disposed in the space formed by the removal of the other collar member.

(9) The pneumatic tire according to any one of the above-described (1) to (8), wherein an object comprising a second member of the mechanical fastener that engages with the first member on the tire inner surface is fixed on the tire inner surface by engagement of the first member and the second member.

(10) The pneumatic tire according to the above-described (9), wherein the recess is formed in the tire inner surface around the mechanical fastener member, an outer edge line of the object being positioned within the outer edge line of the recess at all positions when the tire inner surface is viewed in plan from vertically above the tire inner surface.

(11) The pneumatic tire according to the above-described (9) or (10), wherein the object comprising the second member is (a) an electronic circuit comprising a sensor, (b) a balance weight, (c) a run-flat core, (d) an object on which an oxygen scavenger, a drying agent, and/or an ultraviolet light detecting color fixing agent is applied or mounted, (e) a noise absorbing member, or a combination thereof.

(12) The pneumatic tire according to any one of the above-described (1) to (11) used for construction vehicles having a tire external diameter of 0.8 m or greater.

A method of manufacturing the pneumatic tire of the present technology that achieves the aforementioned object has the configuration described in (13) below.

(13) A method of manufacturing a pneumatic tire that comprises a mechanical fastener member on a tire inner surface, the mechanical fastener member corresponding to a first member of a mechanical fastener separable into two members, and the mechanical fastener member being fixed protruding to a tire cavity side, the method comprising the steps of:

disposing the mechanical fastener member on an inner surface of an unvulcanized green tire so as to protrude to a tire cavity side;

disposing a collar member in a space formed between a region approximate to a protruding tip of a protruding portion of the mechanical fastener member and the inner surface of the green tire around the mechanical fastener member to fill the space; and vulcanization molding the green tire;

the collar member being removed in the time after vulcanization molding and before the pneumatic tire comes into use.

According to the present technology of (1), a pneumatic tire provided with a mechanical fastener member for attaching an object to the inner surface of a pneumatic tire is provided. Specifically, the pneumatic tire is provided with the mechanical fastener member bonded to the tire inner circumferential surface with an extremely high bonding strength. As a result, there are less occurrences of separation and the like of the attached object, and the function of the object can be active in a stable manner over an extended period of time.

According to the present technology of (2), although the protruding height of the fastener member is relatively high, a superior pneumatic tire of the present technology can be achieved in which the obtained effects of the present technology are more reliably realized than that of the present technology of (1) described above.

According to the present technology of (3), because an object with a relatively large dimension can be attached to the tire inner surface, a pneumatic tire of the present technology can be achieved in which the effects of the present technology according to (1) can be in practice realized to a higher degree.

According to the present technology of (4), a pneumatic tire of the present technology can be achieved in which the effects of the present technology according to (1) are realized to a higher degree.

According to the present technology of (5), a pneumatic tire of the present technology can be achieved in which the effects of the present technology according to (1) are realized to a higher degree.

According to the present technology of any one of (6) to (8), the effect of the present technology according to (1) can be achieved, and the protruding mechanical fastener is physically protected by the detachable collar member. As a result, damage to and failure of the tire during storage are prevented. Also, when the collar member is disposed prior to vulcanization molding of the pneumatic tire, the collar member can facilitate the effectiveness of the action of the pressure and temperature of the bladder at the region around the base where the mechanical fastener member is attached. Consequently, vulcanization molding at the region of the base where the mechanical fastener member is attached can be increased in effectiveness, allowing for a mechanical fastener member with high fixing strength to be obtained (7), (8). In particular, according to the present technology of (8), a pneumatic tire of the present technology can be achieved that has not just the effects described above, but also the effect of more effectively preventing damage to and failure of the tire during storage by replacing the collar member after vulcanization molding with a collar member made of material more suited to the physical protection of the mechanical fastener member.

According to the present technology of (9), a pneumatic tire is provided in which a desired object is attached to the tire inner surface at a predetermined position with high fixing strength and superior durability. Also, according to the technology of (10), this effect can be obtained regardless of the dimensions of the desired object. Particularly, the effect is significant when the weight or volume of an object with a desired function to be attached to the tire inner surface is, to a certain degree, large.

According to the present technology of (11), a pneumatic tire can be achieved in which each type of object having a desired function is attached to the tire inner surface at a predetermined position with high fixing strength and superior durability.

According to the present technology of (12), a pneumatic tire for construction vehicles can be achieved in which each type of object having a desired function is detachably attached to the tire inner surface at a predetermined position with a high fixing strength and a superior durability. In particular, the effects of the present technology can be sufficiently obtained in light of the importance of continually monitoring and measuring of the air pressure and the like in the tire cavity, due to pneumatic tires of construction vehicles being large in dimension and weight and the construction vehicles also being large in weight.

According to the present technology of (13), a method of manufacturing a pneumatic tire provided with a mechanical fastener member for attaching an object to a tire inner surface is provided, wherein the mechanical fastener member is bonded to the tire inner circumferential surface with an extremely high bonding strength. A tire manufactured by this method is superior in that there are less occurrences of separation and the like of the attached object, and the function of the object can be active in a stable manner over an extended period of time.

BRIEF DESCRIPTION OF DRAWINGS

FIG. 2 is also a cross-sectional view illustrating the state upon vulcanization molding of the tire using a bladder in which a collar member is disposed, upon vulcanization molding, around the mechanical fastener member to be fixed to the tire inner surface in the space formed between a protruding tip of the mechanical fastener member and the tire inner surface around the mechanical fastener member.

FIGS. 9A and 9B are drawings illustrating each example configuration of the collar member that can be used in the method of manufacturing the pneumatic tire of the present technology. In FIGS. 9A and 9B, the top drawing is a plan view and the bottom drawing is a longitudinal cross-sectional view.

DETAILED DESCRIPTION

A detailed explanation of the pneumatic tire of the present technology will be given below.

Figure 1:
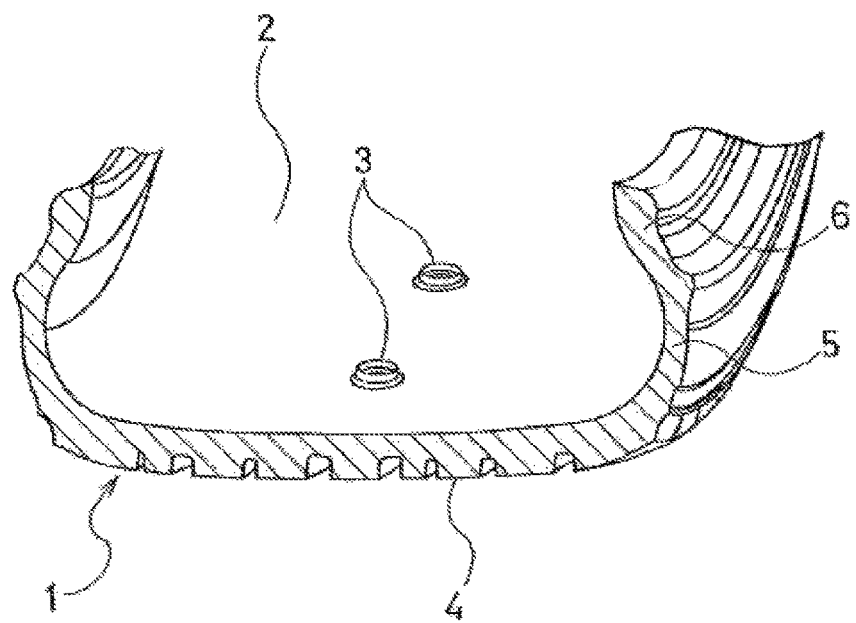
FIG. 1 is a perspective view of a partial cross section illustrating an embodiment of the pneumatic tire of the present technology.

As illustrated in FIG. 1, the pneumatic tire 1 of the present technology comprises a mechanical fastener member 3 that is a first member of a mechanical fastener separable into two members. The mechanical fastener member 3 is disposed on the tire inner surface 2 and fixed protruding to the tire cavity side. The fixing strength of the mechanical fastener member 3 is from 0.1 to 100 (N/mm$^2$). In FIG. 1, 4 denotes a tread portion; 5 denotes a sidewall portion; and 6 denotes a bead portion.

In the present technology, "mechanical fastener" refers to a pair of fastener members configured so that the pair of fastener members can be separated into two fastener members and can be physically re-engaged, and so that this engaging and separating can be freely repeated. This configuration may be basically similar to those of Japanese Unexamined Patent Application Publication Nos. 2012-25318A, 2012-25319A and 2012-240465A described above.

Exemplary types of such a mechanical fastener are those known as "hooks" or "snaps". Specific examples of products in the clothing industry that are generally included as mechanical fasteners are snap buttons, ring snaps, ring hooks, American snaps, American hooks, eyelet hooks, spring hooks, and jumper hooks. Such mechanical fasteners differ from surface fasteners in that while an area of the engaging part of a surface fastener is unlimited in the entire area, the area of the engaging part of a mechanical fastener is small (for example, preferably from about 1 to 115 mm$^2$ and more preferably from about 4 to 90 mm$^2$). In other words, mechanical fasteners are point fasteners. In other words, even when engaged at a small area of from about 1 to 115 mm$^2$ for example, due to a mechanical male-female structure or the like, strong engaging is achieved. Thus, a conventional structure for the mechanical fastener may be used. The mechanical fastener can be formed from materials such as metals, as well as synthetic resins, hard rubbers, and the like.

The advantages of using such mechanical fasteners are basically the same as that described in the explanation of the conventional art.

In the present technology, the mechanical fastener member 3 may, for example, be attached approximate to the tire equator of the tire inner surface as illustrated in FIG. 1, but is not particularly limited thereto. The mechanical fastener member 3 may also be disposed on the tire inner surface approximate to the bead portion 6 or the sidewall portion 5, where centrifugal forces due to tire rotation and repeated deformation of the tire inner surface accompanying tire rolling motion have less of an impact than the impact on such a tread portion 4. The present inventors believe that a fixing strength of from 0.1 to 100 (N/mm$^2$) is sufficient for a mechanical fastener member 3 to be applied to the majority of cases of attachment-fixing of an object to be attached in a tire cavity. A mechanical fastener member 3 with a fixing strength of less than 0.1 cannot be applied to the attachment of a heavy object. Also, a mechanical fastener member 3 with a fixing strength greater than 100 would require the portion of the tire structure where it is fixed to have localized increased rigidity. As a result of this configuration, rigidity in the circumferential direction of the tire and consequently uniformity would decrease. Alternatively, if the rigidity all around the tire was increased, manufacturing costs would increase unnecessarily. Both cases are not preferable. To further ensure the effects of the technology described above are obtained, the fixing strength is preferably in a range of 0.2 to 50 (N/mm$^2$).

The method of obtaining the main characteristic of the pneumatic tire of the present technology, in other words the mechanical fastener member 3 with a fixing strength of from 0.1 to 100 (N/mm$^2$) described above, is not particularly limited. However, the main characteristic can be achieved by the special method of vulcanization molding the pneumatic tire described in detail below. An outline of the method is described below.

Specifically, by providing the mechanical fastener member 3 on a green tire and simply performing vulcanization molding of a pneumatic tire using a bladder in a conventional manner, a high fixing strength cannot be obtained. This is considered to be due to the protruding portion of the mechanical fastener member 3 causing the actions of the bladder (pressure, temperature) to be insufficient at some portions (the portion around the base of the mechanical fastener member 3), and as a result, causing vulcanization bonding at that region is insufficient. This phenomenon is explained with reference to FIG. 3. When space X, which suppresses the actions of a bladder 8, is formed at region Y around the base of the mechanical fastener member 3, and the vulcanization molding at this region of the tire inner surface is insufficient. This causes high fixing strength to be unobtainable. In particular, when the protruding height H of the mechanical fastener member 3 is large, this phenomenon is significant. Also, the bladder may be damaged where the mechanical fastener member 3 is located, which may also lead to problems in the vulcanization molding.

Figure 2:
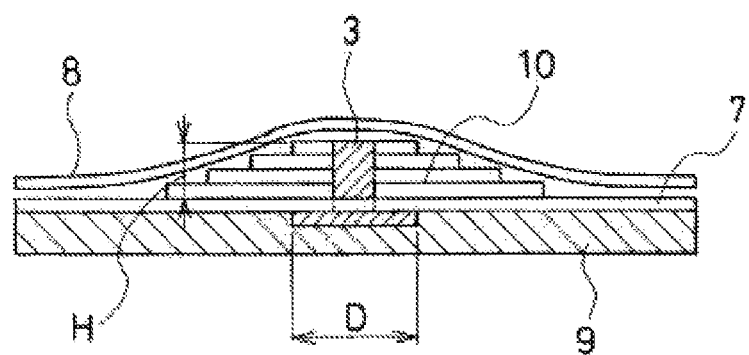
FIG. 2 is a model diagram for explaining an example of a method of manufacturing the pneumatic tire of the present technology.
Figure 3:
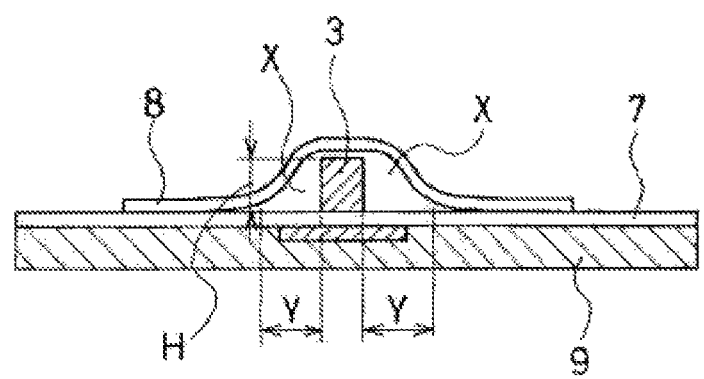
FIG. 3 is a cross-sectional view for comparison to the example of a method of manufacturing the pneumatic tire of the present technology illustrated in FIG. 2. The cross-sectional view illustrates the state around a mechanical fastener member and the relationship of a bladder thereto in a method of manufacturing a pneumatic tire provided with a conventional mechanical fastener member.
Figure 4A:
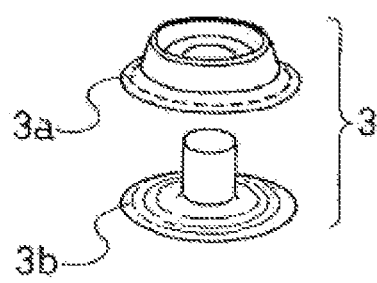
FIGS. 4A and 4B are perspective external model diagrams for explaining an exemplary form of a first member of a mechanical fastener separable into two members used in the pneumatic tire of the present technology, and for explaining how the first member is constituted by two components.
Figure 4B:
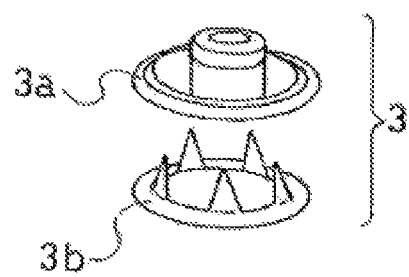
Figure 7:
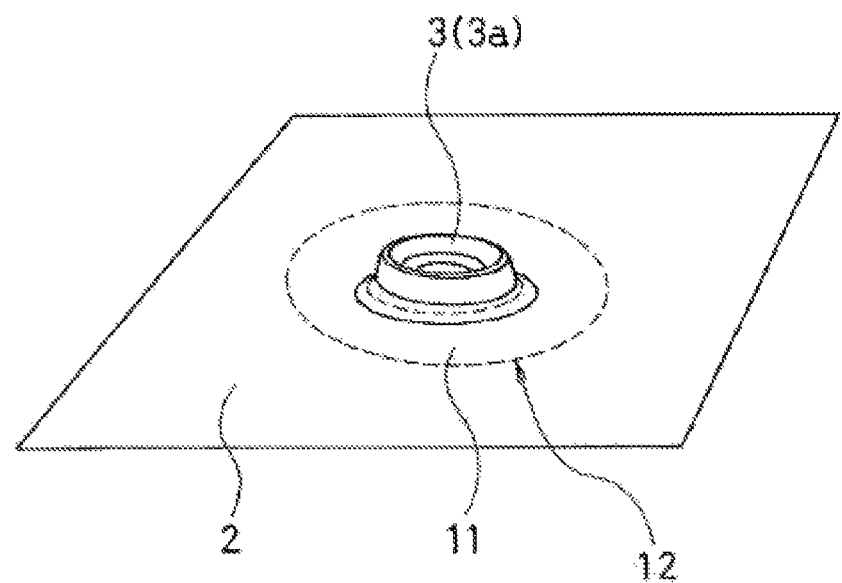
FIG. 7 is an enlarged view for explaining an embodiment of the pneumatic tire of the present technology and illustrates a main portion around the mechanical fastener member provided on the tire inner surface.

In light of the above, the present inventors discovered that by disposing a collar member 10 in the above-described space X, as illustrated in FIG. 2, and performing vulcanization molding, pressure and heat can be sufficiently transmitted from the bladder to the region around the base of the mechanical fastener member 3, and formation of a mechanical fastener member 3 with high fixing strength can be achieved. In FIGS. 2 and 3, 7 denotes a tire structural member or a tire reinforcing member, 8 denotes a bladder, 9 denotes an innerliner, and 10 denotes a collar member. It is important that the collar member 10 is formed from a material that can sufficiently transmit the pressure and heat from the bladder to the green tire to be vulcanization molded (details described below).

The effects of the present technology are particularly significant when the bottom portion of the mechanical fastener member 3 is embedded in the tire inner surface, and the mechanical fastener member 3 has a protruding height H from the tire inner surface of 3 mm or greater and a maximum diameter D of 8 mm or greater. A mechanical fastener member 3 with a protruding height H of 3 mm or greater significantly achieves the effects of using the collar member 10. However, when the maximum diameter D is less than 8 mm, the mechanical fastener member 3 lacks the stability required to support a high protruding height. As a result, a mechanical fastener member 3 with high fixing strength tends to be difficult to obtain and is thus not preferable.

Figure 5:
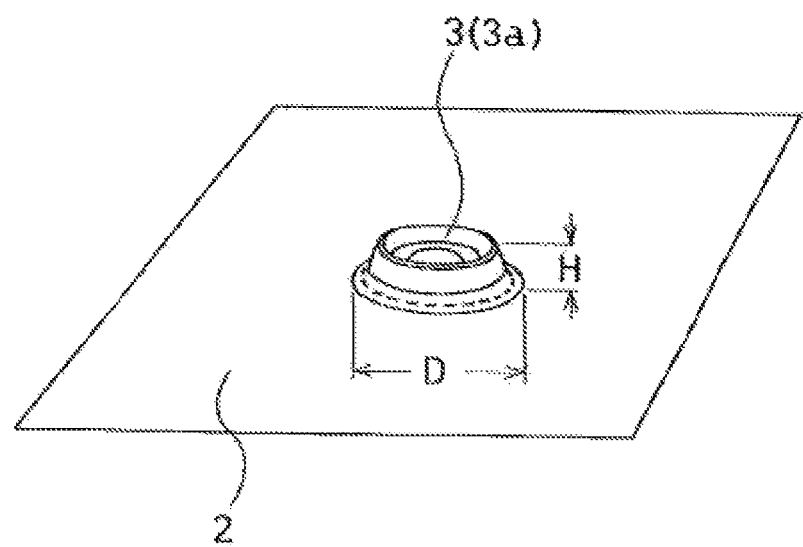
FIG. 5 is an enlarged view for explaining an embodiment of the pneumatic tire of the present technology and illustrates a main portion around the mechanical fastener member provided on the tire inner surface.
Figure 6A:
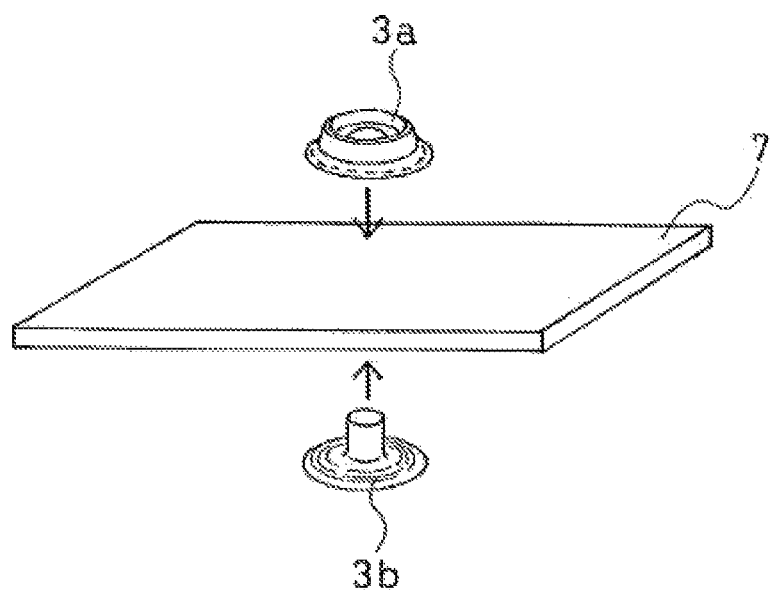
FIGS. 6A and 6B are enlarged views illustrating a main portion for explaining an embodiment of the pneumatic tire of the present technology, and for explaining the state in which the two components illustrated in FIGS. 4A and 4B sandwich a tire member or a tire reinforcing member and fix together to compose the first member.
Figure 6B:
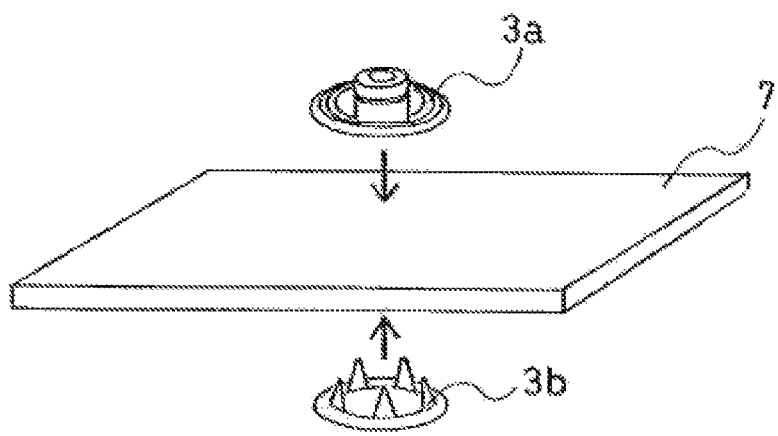

In the present technology, the mechanical fastener member 3 is preferably made of two or more components 3a, 3b, as illustrated by the exemplary configurations of FIGS. 4A to 6B. Also, the two or more components 3a, 3b preferably form the mechanical fastener member 3 by being fixed together and sandwiching the tire member or the tire reinforcing member 7 fixed on the tire, and the mechanical fastener member 3 is preferably fixed to the tire member or tire reinforcing member 7 fixed to the tire by vulcanization bonding. This is because the mechanical bonding strength between the components 3a, 3b enhances the fixing strength of the mechanical fastener member 3 to the tire member or tire reinforcing member 7 fixed to the tire. The two components 3a and 3b are fixed together integrally and form the first member of the pair of mechanical fastener members 3. As illustrated in FIG. 5, the component 3a is mainly exposed on the tire inner surface 2.

Here, "tire reinforcing member 7" refers to a component of the tire made of rubber, resin, or the like, and specifically refers to an innerliner, a carcass, or the like. Alternatively, a rubber layer exclusively for being sandwiched between the component 3a and the component 3b of the fastener, a rubberized reinforcing fiber layer or resin layer, or a plurality of laminated layers thereof forming a reinforcing layer may be additionally provided on the tire inner surface as the tire reinforcing member 7. Such a configuration is preferable because, generally, air shutoff performance in the tire is enhanced.

Figure 10A:
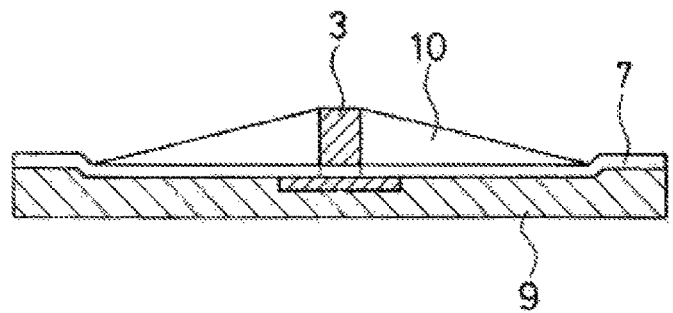
FIGS. 10A and 10B are enlarged side views for explaining an embodiment of the pneumatic tire of the present technology and illustrate a main portion around the mechanical fastener member provided on the tire inner surface, in particular a configuration in which a recessed portion is formed around the mechanical fastener member.
Figure 10B:
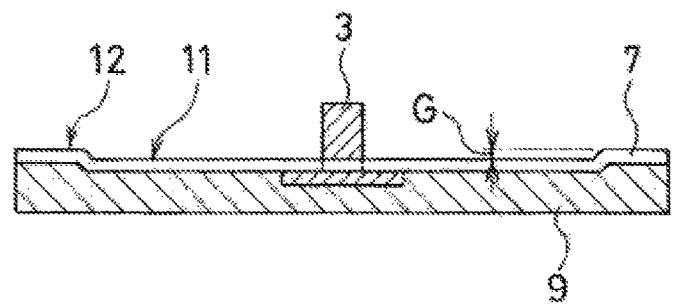

In the present technology, the tire inner surface 2 preferably has a recessed portion 11 formed around the mechanical fastener member 3, as illustrated in FIG. 7. In FIG. 7, 12 denotes the outer edge line of the recessed portion 11. The recessed portion 11 can be formed by using the collar member 10 and applying higher pressure to the desired region than to the surrounding area, as illustrated in FIG. 10A. As the tire inner surface is curved, when an object to be attached has a flat bottom surface, the two surfaces can interfere with each other. By forming the recessed portion 11 around the mechanical fastener member 3, this interference is effectively avoided. The recess preferably has a recess depth G of from 0.2 mm to 3 mm, as illustrated in FIG. 10B. Also, the recess preferably has a flat surface without curves to prevent interference.

When the tire inner surface is viewed in plan from vertically above the tire inner surface, the entire of the recessed portion 11 is preferably located within the outer edge line of the tire reinforcing member 7 (see FIGS. 6A and 6B) so as to maintain a high fixing strength.

The above-described collar member 10 used in the vulcanization molding of the pneumatic tire of the present technology is removed from the tire after the vulcanization molding is completed. In other words, the collar member is not a constituent member of the tire when the tire is in use. However, in order to physically protect a protruding tip of the mechanical fastener member and/or the entire mechanical fastener member, a removable collar member may be disposed in the space formed between the protruding tip of the mechanical fastener member and the tire inner surface around the mechanical fastener member for the distribution or storage of the tire.

When a collar member is used for distribution or storage, the same collar member used for vulcanization molding of the pneumatic tire may be used, or a different collar member ideal for protection during distribution or storage may be used.

To achieve a high performance pneumatic tire, the pneumatic tire of the present technology preferably comprises an object with a specific function provided with a second member of a mechanical fastener that engages with the first member 3 of a mechanical fastener located on the tire inner surface, the two fastener members engaging to fix the object to the tire inner surface.

The object may be selected to correspond with desired characteristics, and the object is not particularly limited. Preferable examples of such an object include any one or a combination of (a) an electronic circuit including a sensor, (b) a balance weight, (c) a run-flat core, (d) an object on which an oxygen scavenger, a drying agent, and/or an ultraviolet light detecting color fixing agent is applied or mounted, and (e) a noise absorbing member.

When the tire inner surface is viewed in plan from vertically above the tire inner surface, the object and the recess of the tire inner surface around the mechanical fastener member described above preferably have a relationship in which the outer edge line of the object is positioned within the outer edge line 12 of the recess (see FIG. 10B) at all positions. This is to prevent any interference between the attached object and the tire inner surface, even if the object is rotated about the fastener member. Here, "outer edge line of the object" refers to the outermost edge line of, for example, a pedestal, case, or housing if the object is housed therein and then attached. The distance between the outermost edge line of the object and the outer edge line of the recess is at a minimum preferably not less than 2 mm.

The pneumatic tire of the present technology is in practice preferably a tire for construction vehicles with a tire external diameter of 0.8 m or greater. This is because, although air pressure meters are often mounted onto wheels to monitor and check air pressure in the tire cavity and the like, the wheels used therefor have a shape that is difficult to attach air pressure meters to.

The method of manufacturing the pneumatic tire of the present technology, as described above, uses a collar member when setting the mechanical fastener member and vulcanization molding the tire.

Figure 8A:
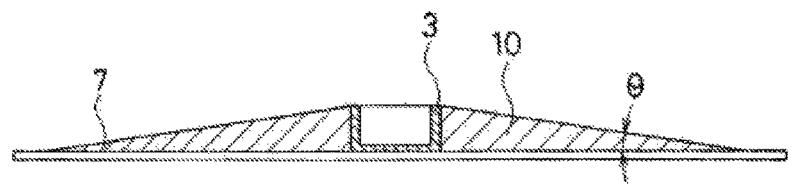
FIGS. 8A to 8D are longitudinal cross-sectional views illustrating each example configuration of the collar member that can be used in the method of manufacturing the pneumatic tire of the present technology.
Figure 8B:
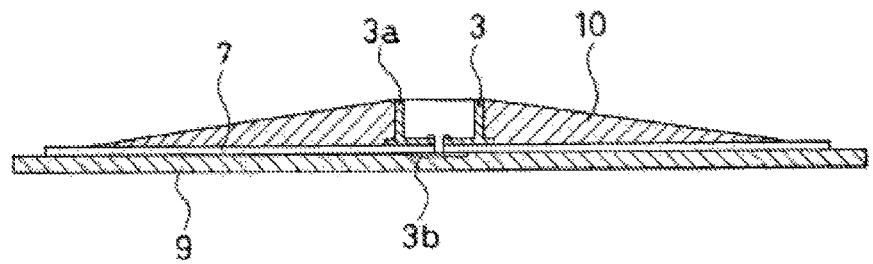
Figure 8C:
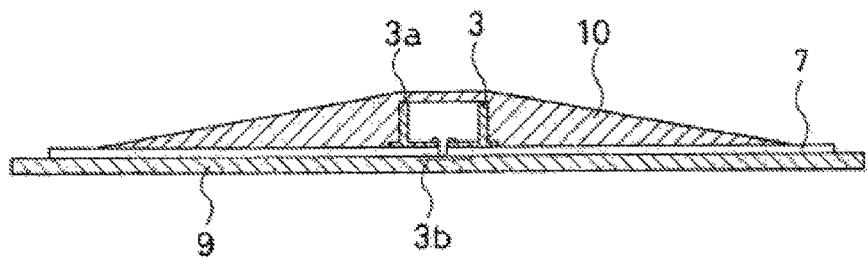
Figure 8D:
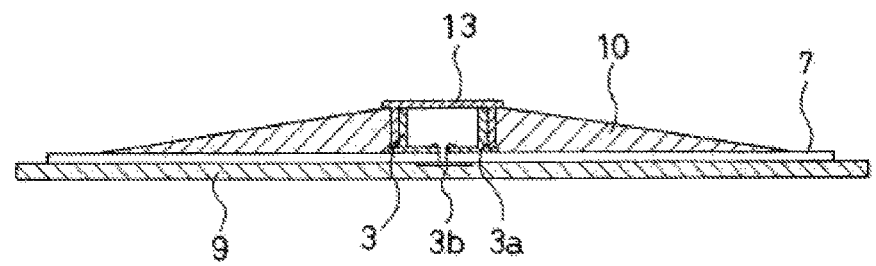

Specifically, the method of manufacturing comprises the steps of disposing the mechanical fastener member 3 on the inner surface of an unvulcanized green tire so as to protrude to the tire cavity side, disposing a collar member 10 in a space formed between a region approximate to the protruding tip of the protruding portion of the mechanical fastener member 3 and the inner surface of the green tire around the mechanical fastener member 3 to fill the space, and vulcanization molding the green tire. Furthermore, the collar member 10 is removed in the time after vulcanization molding and before the pneumatic tire comes into use. FIGS. 8A to 8D are model diagrams illustrating disposed collar member 10 of each configuration. FIG. 8A illustrates a configuration in which the collar member is disposed with the mechanical fastener member 3 located on the tire structural member or tire reinforcing member 7. FIG. 8B illustrates a configuration in which the mechanical fastener member 3 made of two components is formed sandwiching the tire structural member or the tire reinforcing member 7, and the innerliner 9 is also vulcanization bonded. FIG. 8C illustrates a configuration in which the collar member 10 covers the apex of the mechanical fastener member 3 of the configuration illustrated in FIG. 8B. FIG. 8D illustrates a configuration in which the collar member 10 is used formed integrally with the second member 13 of the mechanical fastener that engages with the first member 3 of the mechanical fastener on the tire inner surface side. The configurations of FIGS. 8C and 8D have advantages such as of stopping foreign material from entering the engaging recessed portion of the mechanical fastener member 3.

Figure 11:
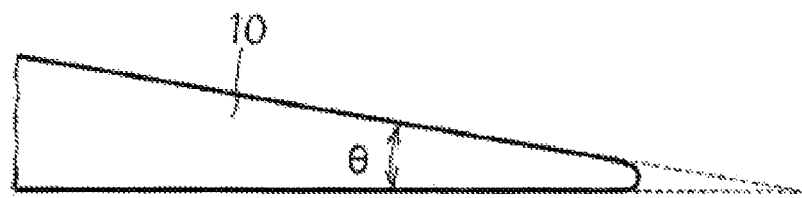
FIG. 11 is a cross-sectional view for explaining, using a model, about a preferable form of the collar member that can be used in the method of manufacturing the pneumatic tire of the present technology.

The collar member 10 preferably has a low conical shape with gentle slopes that taper to the center (apex) of the mechanical fastener member 3. The collar member 10 illustrated is FIG. 8A preferably has an angle θ of inclination of about from 3 to 20 degrees, but is not particularly limited thereto. Note that the angle θ of inclination of the collar member 10 is an angle obtained at a relatively central position that does not include the shape of the tip, as illustrated in FIG. 11. In order to transmit the pressure of the bladder to the tire, the material of the collar member 10 is preferably made of metal, synthetic resin, laminated release paper, or the like. From the perspective of handleability including ease of removal, the present inventors believe that material made of fluororesin (for example, Teflon (registered trademark)) is preferable. Also, the material preferably has a thermal conductivity of from 0.1 to 300 W/mK to ensure heat from the bladder transmits to the tire.

The mechanical fastener member 3 preferably has the base portion thereof embedded in the tire inner surface, as illustrated in FIG. 2, FIGS. 10A and 10B, and the like. This configuration is preferable because an increased fixing strength can be obtained by vulcanization bonding, and durability is dramatically increased. The protruding height H of the mechanical fastener member 3 from the tire inner surface is preferably from 3 mm to 15 mm, as described above, and the maximum diameter D is preferably 8 mm or greater. This preferable configuration allows the effects of the technology to be significant.

FIGS. 9A and 9B are plan views for explaining each configuration of the collar member 10 which can be used in the method of manufacturing the pneumatic tire of the present technology. In FIGS. 9A and 9B, the top drawing is a plan view and the bottom drawing is a longitudinal cross-sectional view. In a plan view, FIG. 9A is a view illustrating the circular collar member and FIG. 9B is a view illustrating a rounded-square collar member. Also, a collar member with shape such as a regular polygon may be used.

EXAMPLES

Below, the pneumatic tire and the method of manufacturing a pneumatic tire of the present technology based on working examples are explained.

Note that in the present technology, the fixing strength of the mechanical fastener member is measured by the following method.

(a) Method of Measuring the Fixing Strength of the Mechanical Fastener Member

Figure 12A:
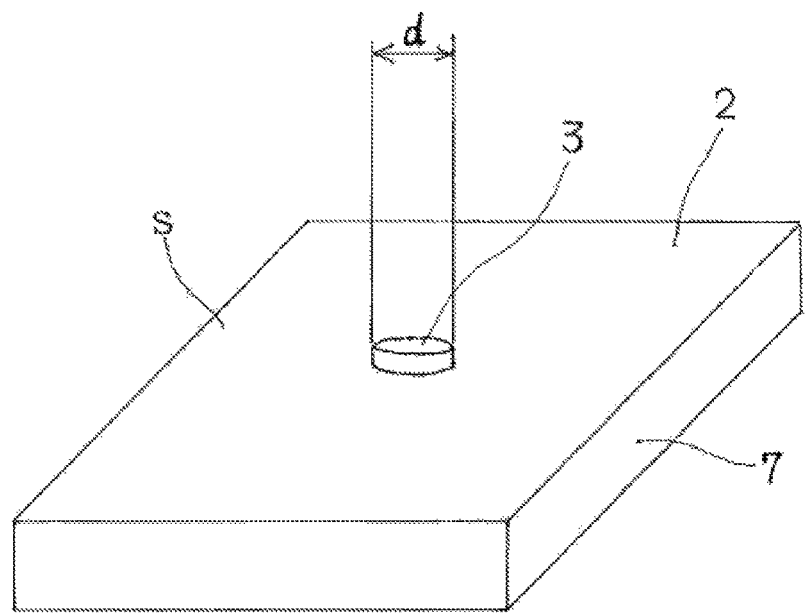
FIGS. 12A and 12B are perspective views for explaining the method of measuring fixing strength of the mechanical fastener member employed in the present technology.
Figure 13A:
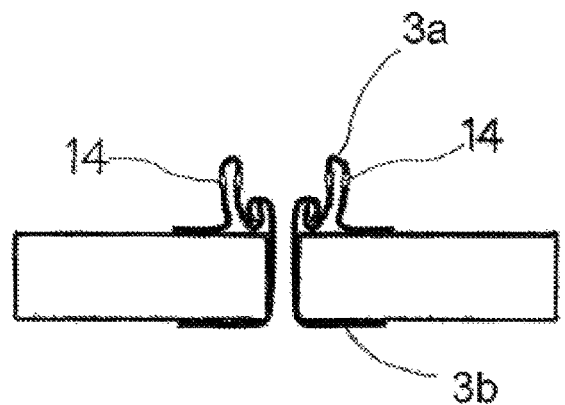
FIGS. 13A and 13B are schematic views for explaining the method of measuring fixing strength of the mechanical fastener member employed in the present technology. A method in which a shaft shaped jig for a tensile test is engaged with the mechanical fastener member is illustrated.
Figure 13B:
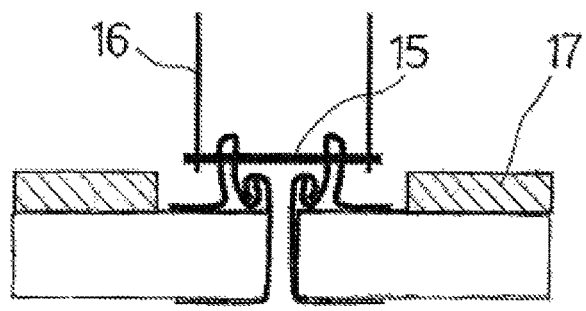
Figure 14:
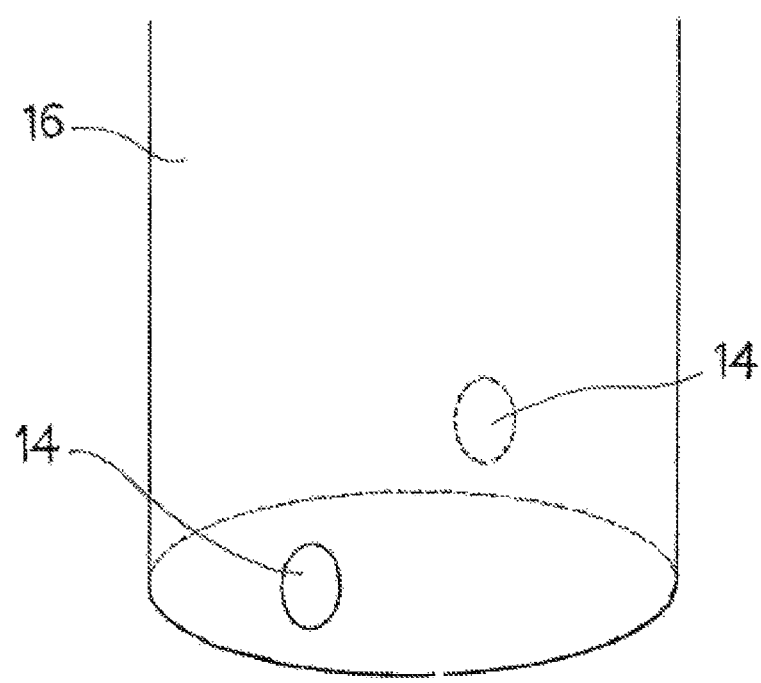
FIG. 14 is a schematic view for explaining the method of measuring fixing strength of the mechanical fastener member employed in the present technology. An example configuration of the shaft shaped jig for a tensile test engaged with the mechanical fastener member is illustrated using a model.

A green tire in which the mechanical fastener member 3 is disposed is vulcanized to manufacture a tire according to the present technology. Then, a portion of the tire around the mechanical fastener member 3 is cut out, which is a test sample S (see FIG. 12A). A pair of holes 14 (see FIG. 13A) is opened in the mechanical fastener member 3 in the test sample and a rod shaped piercing jig 15 is passed through the pair of holes 14. A shaft shaped jig for a tensile test 16 is attached to the test sample via the piercing jig 15 (see FIG. 13B). The shaft shaped jig for a tensile test 16 has the configuration illustrated in the model diagram of FIG. 14 and includes the pair of holes 14 located approximate to the cylindrical end portion of the shaft shaped jig for a tensile test 16.

Figure 12B:
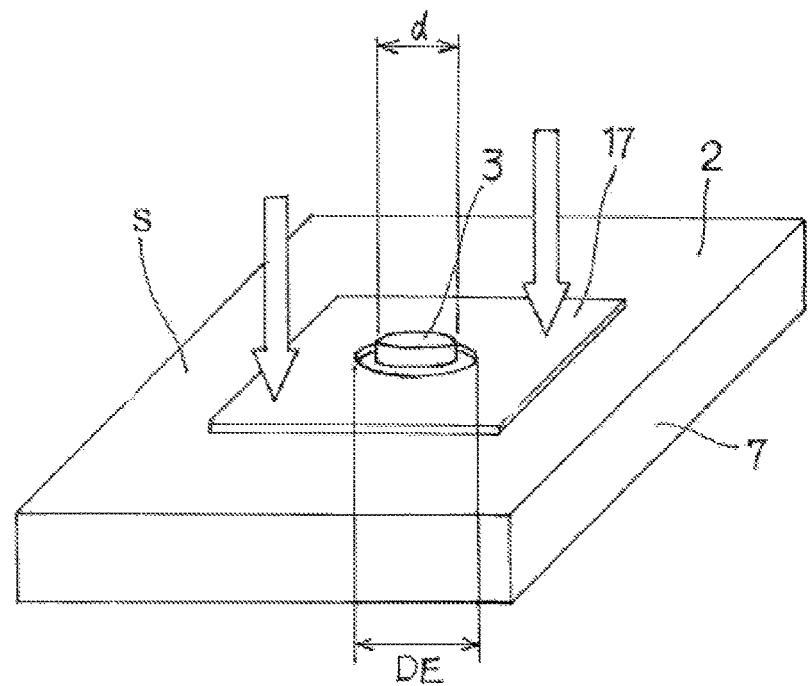

When pulling out of the mechanical fastener member 3 via the shaft shaped jig for a tensile test 16 is performed, a fixing board 17 is disposed on the tire inner surface 2 around the mechanical fastener member 3, as illustrated in FIG. 12B, and the strength at break is obtained when the mechanical fastener member 3 is pulled out in the vertical direction in respect to the fixing board 17. The pulling speed is 500±50 mm/min.

Note that the fixing board 17 thus used has a hole with a diameter DE of from 1.30 to 1.35 times the diameter d of the protruding portion of the mechanical fastener 3. When pulling out of the mechanical fastener member 3 described above is performed, the fixing board 17 is firmly fixed so as to not rise. In such a manner, the shaft shaped jig for a tensile test 16 is pulled vertically, and the tensile force at the time the mechanical fastener member 3 separates from the tire structure is taken as the strength at break.

The obtained value of the strength at break is divided by the maximum cross-sectional area of the mechanical fastener member 3 (component 3a or 3b) to give the value per unit cross-sectional area (N/mm$^2$). The same test is performed on three test samples, with the average value taken as the fixing strength (N/mm$^2$).

Note that the method of measuring described above is merely a detailed example of a method of measuring. As long as the above-described tensile testing method is used as a base, the method may be made more suitable by changing the shape of the mechanical fastener and the like.

Working Examples 1 to 3 and Comparative Examples 1 and 2

Figure 15:
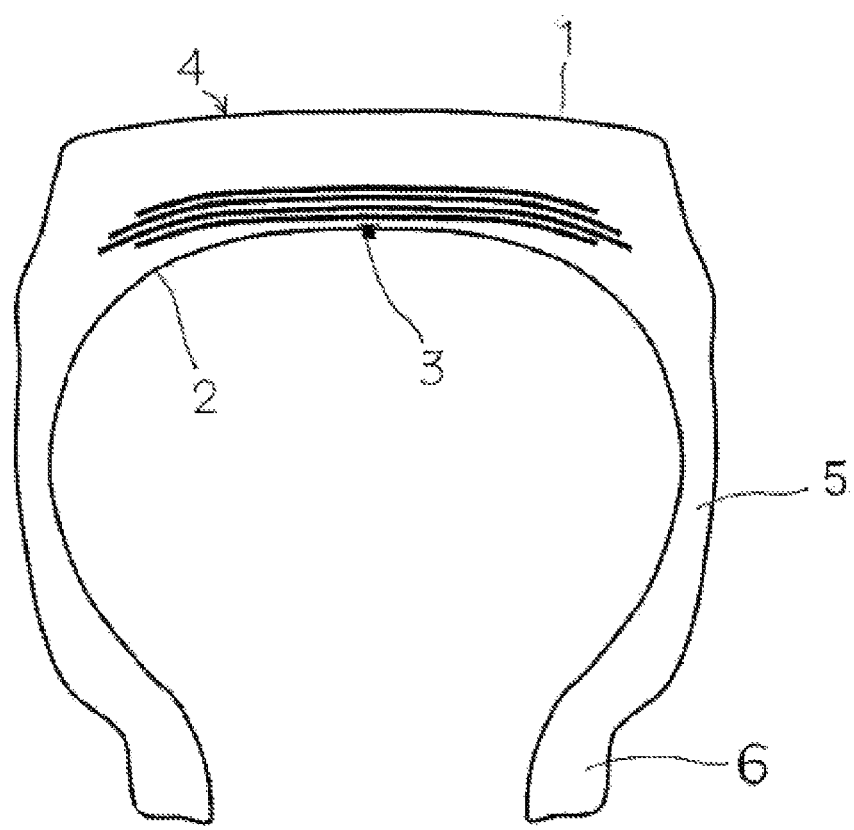
FIG. 15 is a tire meridian direction cross-sectional view illustrating, using a model, the fixing position of the mechanical fastener member employed in the examples.

Using a mechanical fastener member with a configuration illustrated in FIG. 8A or 8B, one mechanical fastener member 3 was disposed on the equator portion of the inner circumferential surface of the tread portion of each pneumatic tire for construction vehicles, as illustrated in the model diagram of FIG. 15, and vulcanization bonded by vulcanization molding of the tires.

In Working Examples 1 to 3, a collar member (made of fluororesin (Teflon®)) having the configuration illustrated in FIG. 9A was used. In Comparative Examples 1 and 2, no collar member was used, and the other components were vulcanization bonded in the vulcanization molding of the tires in a manner similar to that of Working Examples.

The protruding height H (mm) from the tire inner surface and maximum diameter D (mm) of the mechanical fastener member of each test tire is shown in Table 1.

The results of the measurement of the fixing strength of the mechanical fastener member for each obtained test tire is also shown in Table 1.

TABLE 1

|  | Comparative Example 1 | Comparative Example 2 | Working Example 1 | Working Example 2 | Working Example 3 |
|---|---|---|---|---|---|
| Mechanical fastener member | FIG. 8A | FIG. 8A | FIG. 8A | FIG. 8A | FIG. 8B |
| Reinforcing member used? | No | No | No | No | Yes |
| Collar member used? | No | No | Yes | Yes | Yes |
| Protruding height H of mechanical fastener member (mm) | 2.5 | 5.0 | 5.0 | 5.0 | 5.0 |
| Maximum diameter D of mechanical fastener member (mm) | 5.0 | 8.5 | 8.5 | 14.0 | 14.0 |
| Fixing strength of mechanical fastener member (N/mm$^2$) | 0.07 | 0.08 | 0.16 | 0.22 | 2.8 |

The present inventors believe that a fixing strength of 0.1 N/mm$^2$ or greater is sufficient for application to the majority of cases of attachment-fixing of an object to be attached in the tire cavity, and furthermore that a fixing strength of 0.2 N/mm$^2$ or greater is sufficient for application to almost all cases of attachment-fixing of an object to be attached in the tire cavity.

As can be seen from the results shown in Table 1, the pneumatic tires according to the present technology having such a fixing strength are superior tires.

The invention claimed is:

1. A pneumatic tire comprising a detachable collar member disposed around a mechanical fastener member in a space formed between a protruding tip of the mechanical fastener member and a tire inner surface around the mechanical fastener member, the mechanical fastener member being on the tire inner surface, the mechanical fastener member corresponding to a first member of a mechanical fastener separable into two members, and the mechanical fastener member being fixed protruding to a tire cavity side; wherein the mechanical fastener member has a fixing strength of from 0.1 to 100 mm $^2$.

2. The pneumatic tire according to claim 1, wherein a bottom portion of the mechanical fastener member is embedded in the tire inner surface, and the mechanical fastener member has a protruding height from the tire inner surface of 3 mm or greater and a maximum diameter of 8 mm or greater.

3. The pneumatic tire according to claim 2, wherein a recess is formed in the tire inner surface around the mechanical fastener member.

4. The pneumatic tire according to claim 3, wherein the mechanical fastener member comprises two or more components, the two or more components forming the mechanical fastener member by being fixed together and sandwiching a tire member or a tire reinforcing member fixed to the tire; and the mechanical fastener member is fixed to the tire member or the tire reinforcing member fixed to the tire by vulcanization bonding.

5. The pneumatic tire according to claim 4, wherein the mechanical fastener member comprises the two or more components, the two or more components forming the mechanical fastener member by being fixed together and sandwiching the tire reinforcing member fixed to the tire; and the recess is formed in the tire inner surface around the mechanical fastener member, the entire recess being positioned within an outer edge line of the tire reinforcing member when the tire inner surface is viewed in plan from vertically above the tire inner surface.

6. The pneumatic tire according to claim 5, wherein the collar member is disposed prior to vulcanization molding of the pneumatic tire, and the pneumatic tire is vulcanization molded in a state in which the collar member is disposed.

7. The pneumatic tire according to claim 5, wherein an other collar member is disposed in the space prior to vulcanization molding of the pneumatic tire and removed after the vulcanization molding of the pneumatic tire, the collar member being disposed in the space formed by the removal of the other collar member.

8. The pneumatic tire according to claim 7, wherein an object comprising a second member of the mechanical fastener that engages with the first member on the tire inner surface is fixed on the tire inner surface by engagement of the first member and the second member.

9. The pneumatic tire according to claim 1, wherein a recess is formed in the tire inner surface around the mechanical fastener member.

10. The pneumatic tire according to claim 1, wherein the mechanical fastener member comprises two or more components, the two or more components forming the mechanical fastener member by being fixed together and sandwiching a tire member or a tire reinforcing member fixed to the tire; and
the mechanical fastener member is fixed to the tire member or the tire reinforcing member fixed to the tire by vulcanization bonding.

11. The pneumatic tire according to claim 1, wherein the mechanical fastener member comprises the two or more components, the two or more components forming the mechanical fastener member by being fixed together and sandwiching a tire reinforcing member fixed to the tire; and
the recess is formed in the tire inner surface around the mechanical fastener member, the entire recess being positioned within an outer edge line of the tire reinforcing member when the tire inner surface is viewed in plan from vertically above the tire inner surface.

12. The pneumatic tire according to claim 1, wherein the collar member is disposed prior to vulcanization molding of the pneumatic tire, and the pneumatic tire is vulcanization molded in a state in which the collar member is disposed.

13. The pneumatic tire according to claim 1, wherein an other collar member is disposed in the space prior to vulcanization molding of the pneumatic tire and removed after the vulcanization molding of the pneumatic tire, the collar member being disposed in the space formed by the removal of the other collar member.

14. The pneumatic tire according to claim 1, wherein an object comprising a second member of the mechanical fastener that engages with the first member on the tire inner surface is fixed on the tire inner surface by engagement of the first member and the second member.

15. The pneumatic tire according to claim 14, wherein the object comprising the second member is (a) an electronic circuit comprising a sensor, (b) a balance weight, (c) a run-flat core, (d) an object on which an oxygen scavenger, a drying agent, and/or an ultraviolet light detecting color fixing agent is applied or mounted, (e) a noise absorbing member, or a combination thereof.

16. The pneumatic tire according to claim 1 used for construction vehicles having a tire external diameter of 0.8 m or greater.

17. A pneumatic tire comprising:
a mechanical fastener member on a tire inner surface, the mechanical fastener member corresponding to a first member of a mechanical fastener separable into two members, and the mechanical fastener member being fixed protruding to a tire cavity side; wherein
the mechanical fastener member has a fixing strength of from 0.1 to 100 N/mm$^2$;
an object comprising a second member of the mechanical fastener that engages with the first member on the tire inner surface is fixed on the tire inner surface by engagement of the first member and the second member; and
the recess is formed in the tire inner surface around the mechanical fastener member, an outer edge line of the object being positioned within the outer edge line of the recess at all positions when the tire inner surface is viewed in plan from vertically above the tire inner surface.

18. A method of manufacturing a pneumatic tire that comprises a mechanical fastener member on a tire inner surface, the mechanical fastener member corresponding to a first member of a mechanical fastener separable into two members, and the mechanical fastener member being fixed protruding to a tire cavity side, the method comprising the steps of:
disposing the mechanical fastener member on an inner surface of an unvulcanized green tire so as to protrude to a tire cavity side;
disposing a collar member in a space formed between a region approximate to a protruding tip of a protruding portion of the mechanical fastener member and the inner surface of the green tire around the mechanical fastener member to fill the space; and
vulcanization molding the green tire;
the collar member being removed in the time after vulcanization molding and before the pneumatic tire comes into use.

* * * * *